United States Patent [19]

Slemon et al.

[11] Patent Number: 5,374,730
[45] Date of Patent: Dec. 20, 1994

[54] PREPARATION OF OMEPRAZOLE AND LANSOPRAZOLE

[75] Inventors: Clarke Slemon, North York; Bob Macel, Thornhill, both of Canada

[73] Assignee: Torcan Chemical Ltd., Aurora, Canada

[21] Appl. No.: 145,572

[22] Filed: Nov. 4, 1993

[51] Int. Cl.$^5$ .......................................... C07D 401/12
[52] U.S. Cl. ................................................... 546/271
[58] Field of Search .................................... 546/271

[56] References Cited

U.S. PATENT DOCUMENTS 4,255,431  3/1981  Janggren et al. .................... 546/271
4,628,098  12/1986  Nohara et al. ....................... 546/271

*Primary Examiner*—Jane T. Fan
*Attorney, Agent, or Firm*—Ridout & Maybee

[57] ABSTRACT

Omeprazole and lansoprazole, which are chemically pyridine-benzimidazole sulfinyl compounds, are produced from the corresponding acetamide-sulfide compounds by a process of oxidation to form the amide sulfinyl compound, followed by alkaline hydrolysis to the sulfinyl carboxylate or salt, and decarboxylation.

6 Claims, No Drawings

PREPARATION OF OMEPRAZOLE AND LANSOPRAZOLE

FIELD OF THE INVENTION

This invention relates to omeprazole and lansoprazole, and more particularly to novel synthetic methods for their preparation.

BACKGROUND OF THE INVENTION AND PRIOR ART

Omeprazole, which has the chemical structural formula:

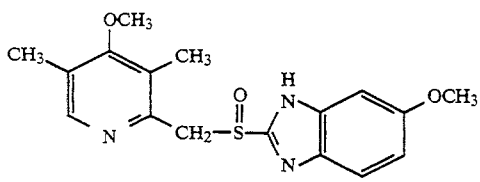

is a known gastric acid secretion inhibiting agent, and is prescribed clinically for the prevention and treatment of gastrointestinal inflammatory diseases in mammals including man, for example gastritis, gastric ulcer and duodenal ulcer. Lansoprazole, which has the chemical structural formula:

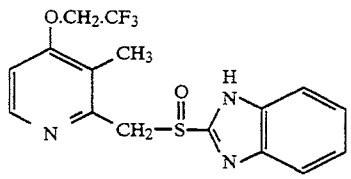

has similar pharmaceutical activity and medicinal uses.

The reported syntheses of omeprazole basically involve the synthesis of the corresponding thioether compound, of the formula:

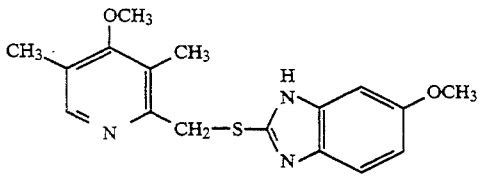

(A)

and its subsequent oxidation to the sulfinyl or sulfoxy compound, omeprazole, by various methods such as reaction with hydrogen peroxide over a vanadium compound catalyst (Canadian Patent 1,263,119 Takeda), reaction with peracids, peresters, ozone, etc. (Canadian patent 1,127,158). Lansoprazole similarly is produced by oxidation of the thioether compound of formula:

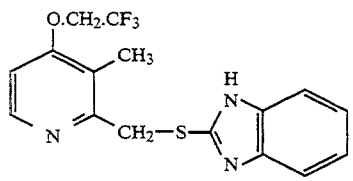

(B)

There are certain disadvantages associated with these processes, largely derived from the nature of the thioether (or sulfide) compound being oxidized.

One of these disadvantages derives from the physical nature of the thioether itself. Under ordinary conditions of temperature and pressure, it is an oil, not a crystalline solid. Accordingly, it is very difficult to purify, since it cannot be subjected to precipitation and crystallization procedures to remove impurities from it. This leads to complications in the processes for purifying the resultant omeprazole.

Another disadvantage associated with both omeprazole and lansoprazole derives from the discolouration of the final product made by oxidation of the thioethers. A red discolouration of the crude products is commonly experienced, and is very difficult to avoid, using this oxidation process. Omeprazole and lansoprazole are inherently unstable molecules in weakly acidic conditions, tending to rearrange to produce annoying highly coloured decomposition impurities.

SUMMARY OF THE INVENTION

It is an object of the present invention to provide a novel process for the preparation of omeprazole and lansoprazole, which overcomes or at least reduces one or more of the disadvantages associated with prior art processes.

According to the present invention, it has been discovered that amide analogues of the thioether compounds A and B, i.e. compounds meeting the general formula:

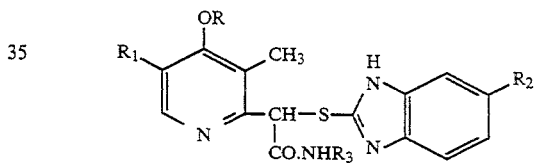

can be readily oxidized to the corresponding sulfinyl compounds. Then the sulfinyl compounds can by hydrolysed in alkaline medium to the corresponding carboxylic acid salts which can be decarboxylated to omeprazole or lansoprazole, as the case may be.

This process offers a number of significant advantages. Some of these relate to the purity in which the final products can be obtained, and the simplicity of the purification procedures which can be adopted to achieve high purity. For example, the amide compounds which are subjected to the oxidation step are crystalline solids, as opposed to oils, so that they are readily purified to a high degree of purity by relatively simply precipitation, crystallization and washing procedures. The carboxylates and carboxylic acid salts which are formed in the next synthetic step after oxidation are water soluble, whereas the final products, omeprazole and lansoprazole, are not. Accordingly, any unreacted residues of these compounds and many other minor impurities in the final products are simply removable by an aqueous washing procedure.

Another significant advantage derived from the process of the present invention is in the avoidance of significant discolouration of the product. In the prior art processes in which a thioether of formula A or B above is subjected to oxidation, mildly acidic conditions are usually required, and a red discolouration of the product is very difficult to avoid. While it is not intended to be bound by any particular theory of the reaction mechanism or by-products responsible for this discolouration, it is believed that interaction of the nitrogen group on the pyridine ring with the S—C—N grouping involving the azole—thioether linkage occurs, creating a conjugated system. Such a conjugated system of S and N atoms would be expected to be highly coloured. These mechanisms have been extensively studied [J. Org. Chem., 1987, 52, 4582–4592].

In the process of the present invention, this problem is not encountered. Acidic conditions for the oxidation and other chemical steps in the synthesis are not necessary, so that the instability leading to the formation of the coloured compounds is largely avoided.

It is further to be noted that the amide compound appears to be unique in the combination of its ability to undergo oxidation from the thioether to the sulfinyl compound, and in its relative ease of subsequent hydrolysis to carboxylate. Analogous thioether compounds substituted at the same positions with other carbonyl groups, for example —COO—lower alkyl, or with a nitrile group, do not oxidize to sulfinyl, at least under acceptable, practical conditions. In addition, the fact that the amide compound according to the invention, following oxidation, can itself be hydrolysed readily to carboxylic acid or salt is surprising in itself. Normally such hydrolyses of compounds of this nature are extremely difficult, if no impossible, to conduct. In the present case, however, substantially complete hydrolysis is achieved, on heating with an aqueous alkali such as sodium hydroxide, in a time of about three hours.

Thus according to one aspect of the present invention, there is provided a process for preparing a pyridine-benzimidazole sulfinyl compound of formula (I):

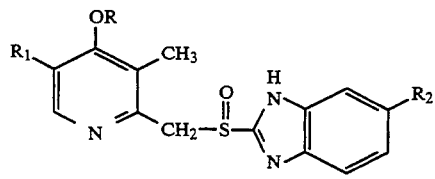

in which either (a) R and $R^1$ are both methyl and $R^2$ is methoxy; or (b) R is 1,1,1-trifluoroethyl and $R^1$ and $R^2$ are both hydrogen, which comprises oxidizing an amide of formula (II):

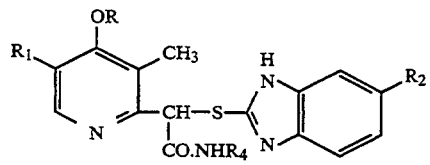

to produce the corresponding amide sulfinyl compound; subjecting the amide sulfinyl compound so formed to alkaline hydrolysis to form a sulfinyl carboxylate, or salt thereof, of formula (III):

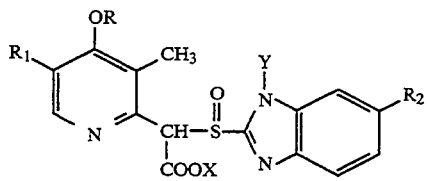

in which X is an alkali metal, Y is hydrogen or a metal, or X and Y together represent a divalent alkaline earth metal; and decarboxylating the sulfinyl carboxylate of formula (III) to form the sulfinyl compound of formula (I); the groups R, $R^1$ and $R^2$ in formula (II) and (III) having the same meanings as given above, and the group R3 in formula (II) above representing hydrogen, lower alkyl or aryl-lower alkyl, optionally further substituted by other functionality to assist in the hydrolysis step.

When choice (a) for the various radicals is made, the end product is omeprazole. When choice (b) is made, the end product is lansoprazole.

The compounds of formula (II), the compounds of formula (III) and the compounds of formula (IV) above are novel chemical compounds, and form further aspects of the present invention.

DESCRIPTION OF THE PREFERRED EMBODIMENTS

The oxidation of the amide of general formula II can be conducted using a wide variety of oxidizing agents, such as those previously proposed for use in oxidizing thioether compounds of formula A in the synthesis of omeprazole. These include the use of hydrogen peroxide as oxidizing agent (with or without catalysts). Other oxidizing agents which can be used include peracids, permanganates, tris(trimethyl) peroxide, N-bromo(-chloro)succinimide, 1,3-dibromo-5,5-dimethylhydantoin, 2-hydroperoxyhexafluoro-2-propanol, iodosyl benzene, manganese (III) acetylacetonate, oxygen (with or without a catalyst), peroxy monosulfate, ruthenium tetroxide, perborate, periodate, acyl nitrates, t-butylhydroperoxide, dimethyl dioxiranes, hypochlorite, cerium ammonium nitrate, 2-nitrobenzenesulfinyl chloride/-potassium superoxide, N-sulfonyloxaziridines, sodium bromite and benzoyl peroxide etc. The oxidation is suitably conducted in an aqueous or polar organic solvent medium, depending upon the choice of oxidizing reagents, and under other conditions such as temperatures and pressures commonly used in organic synthesis when working with the chosen oxidation system. The oxidation process normally leads to the formation of a mixture of the two diastereomers, reflecting the different configuration around the sulphur group. It is unnecessary to separate these isomers.

Particularly preferred among the oxidation systems is the use of hydrogen peroxide with an organic vanadium compound as catalyst, such as vanadyl bis(acetylacetonate), which gives particularly high yields of sulfinyl compound, in relatively short periods of time.

The starting amide material of formula II and the amide-sulfoxide of formula IV and the carboxylate salts of formula III are all solid, crystallizable compounds, so that they can be readily precipitated from solution for ease of purification by simple washing procedures. This is to be contrasted with the prior art processes described above, where the thioether prior to oxidation and the sulfinyl compound after oxidation are oils or low melting solids, and therefore very difficult to purify. The oxidation process is a smooth, clean reaction of one crystalline solid to an isolatable stable sulfoxide, as a mixture of diastereoisomers without the use of acid likely to cause degradation and without significant risk of over-oxidation to lead to discolouration.

The sulfoxides (sulfinyl compounds) so formed are surprisingly stable. One expects sulfoxide compounds with electron attracting groups to undergo spontaneous Pummerer reactions, whereby the oxygen of the sulfoxide group is lost to form a hydroxyl group on the adjacent, carbonyl-carrying carbon atom [Elmer Schroeder and D. M. Dodson, J. Am. Chem. Soc., 84, 1904 (1962)]. This does not appear to occur with the sulfinyl compounds used in the process of the present invention.

The sulfinyl-amide compound of formula II is next subjected to hydrolysis, to form the corresponding carboxylic acid salt. Surprisingly, as noted above, this can be readily accomplished simply by heating with an aqueous alkali, suitably sodium hydroxide solution, so as to obtain the alkali metal salt of the carboxylic acid. Normally one encounters difficulties in achieving hydrolysis of amides of this type, perhaps due to steric hindrance effects or the presence of competitive reactive groups in the molecular structure.

The salt form can be isolated and used in the decarboxylation step or it can be converted in situ. The salt is a solid at ordinary temperatures, so that recovery and purification is relatively easy and straightforward. It is water soluble. Following the recovery of the salt, it can be heated in solution to effect decarboxylation and formation of omeprazole or lansoprazole, as the case may be. In a preferred embodiment of the invention, the salt is not isolated but is warmed in situ in a solvent medium in which it is soluble but in which the product, omeprazole or lansoprazole, is not. The product as it is formed crystallizes out. These final compounds are insoluble in water. The use of the salt form for decarboxylation purposes, with the attendant avoidance of acidification to acidic pHs, removes further risk of discolouration of the end product as discussed above. It appears that the compounds of general formula III have sufficient internal acidity for the decarboxylation reaction, derived from the proton associated with the imidazole ring system, so that neutral or even weakly alkaline conditions can be adopted for this reaction, if desired.

The end product omeprazole or lansoprazole produced by the process of the present invention is easily and simply purified from the residual, unreacted salt, inorganic by-products and other minor by-products by a washing procedure. The desired end products are insoluble in water and lower alkanol solvents, whereas the starting materials and by-products are soluble therein. Consequently, solvent extractions, filtrations and washings are all the steps that are necessary to obtain the end products in highly purified form.

While the acetamide thioether compound of formula II above, the starting material for the process of the present invention, is a novel compound, processes for its preparation will be readily apparent to the skilled organic chemist. These include:

(1) reaction of the appropriately substituted 2-halo-mercapto-benzimidazole with the appropriately substituted 2-methyl-amido-pyridine, thus:

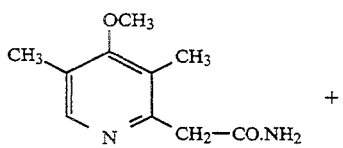

+

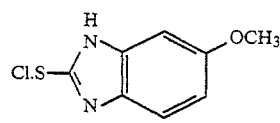

(2) reaction of the appropriately substituted 2-pyridine carboxylate with appropriately substituted 2-S, S-bis(benzimidazole), followed by reaction with ammonia, thus:

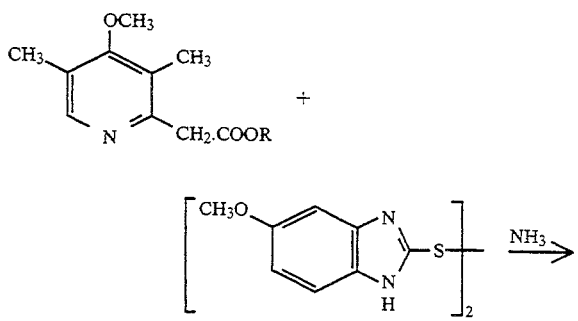

(3) reaction of the appropriately substituted 2-halo-pyridine with the appropriately substituted 2-(methylcarboxylate)-thio-benzimidazole followed by treatment with ammonia, thus:

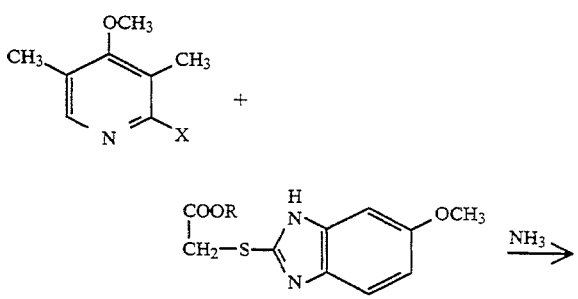

(4) reaction of the appropriately substituted 2-halomethyl-amido-pyridine with the appropriately substituted 2-mercapto-benzimidazole, thus:

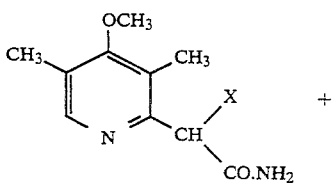

+

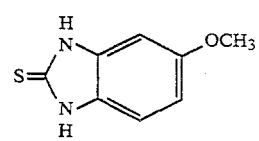

(5) reaction of the appropriately substituted 2-mercaptomethyl-amido pyridine with the appropriately substituted 2-halo-benzimidazole, thus:

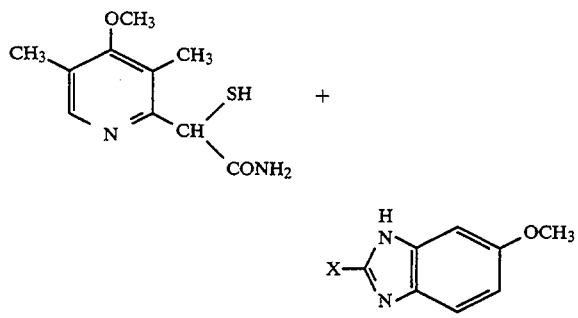

The invention is further described, for illustrative purposes, in the following specific examples.

SPECIFIC DESCRIPTION OF THE MOST PREFERRED EMBODIMENTS

Example 1

A pyridine - thioether - benzimidazole acetamide of formula II, in which R 2 was methoxy, and R and R 1 were both methyl, was oxidized to the sulfinyl (sulfoxide) compound.

92.0 0g of the amide compound substrate and 920 ml acetone were cooled to 0° C. and 0.4 g vanadyl bis(acetylace-tonate) tonate) was added. With stirring at 0° C, 38.6 ml of 30% hydrogen peroxide was added. After stirring for one hour at 0–5°, the mixture was warmed to 20–22° and left stirring for 1 hour. By HPLC, it was determined that less than 1.5% starting material remained. The mixture was cooled to 0° and filtered. The solid was washed with acetone at room temperature until the filtrate was colourless. Finally the solid was washed with a small amount of hexane, and dried at about 40 degrees in vacuum. 86.25g (90%) yield of the sulfoxide compound was obtained, as a mixture of the two stereoisomers.

EXAMPLE 2

The amide sulfoxide product of Example 1, 2 -(5'-methoxy-2-benzimidazolylsulfinyl) 2-(3 , 5-dimethyl-4methoxypyridyl -methoxypyridyl) acetamide sodium salt, was converted to the corresponding acetic acid sodium salt by hydrolysis, and then thermolyzed to give omeprazole.

1.00g of the amide sulfoxide substrate in 5mL of 10% sodium hydroxide was heated under nitrogen in an oil bath at 50 degrees. The transformation from amide to carboxylate was monitored by HPLC. The reaction was essentially complete in three hours. The mixture was acidified with carbon dioxide and the intermediate 2-(5'-methoxy-2'-benzimidazolylsulfinyl)-2-(3,5-dimethyl-4-methoxypyridyl)sodium carboxylate was extracted into 1:1 v/v isopropanol-toluene. The solution was refluxed for 20–30 minutes and the transformation of the carboxylate into omeprazole was monitored by HPLC. The organic mixture was evaporated and the organic materials dissolved in warm isopropanol and filtered to remove inorganic residues. The solution was stirred and cooled to give slow crystallization of a cream coloured solid. The solid was filtered and washed with cold isopropanol and with hexanes. Yield—0.37 g.

EXAMPLE 3

Omeprazole was produced from 2-(5'-methoxy-2-benzimidazolylsulfinyl)-2-(3,5-dimethyl-4-methoxypyridyl) acetic acid dipotassium salt substrate, as follows:

1.0g of substrate was dissolved in 1.0 ml water and mixed with 10 ml of a bisulfite solution pH 4.8, which was prepared by combining 5.0gm of sodium metabisulfite with 75 ml water and 25 ml of methanol. The pH of the total reaction mixture was 7.2. Gradually at room temperature with stirring, 35 drops of glacial acetic acid were added from a disposable pipette, bringing the pH to 4.8. Vigorous gas evolution was observed and the solution became cloudy, then oily. 2.0 ml of methanol was added and the mixture seeded with omeprazole; solid began to precipitate. The reaction was allowed to proceed for 30 minutes. The solid was filtered, washed with water, and then some acetone. Drying gave 0.45 g of off-white omeprazole free of any substantial impurities.

What is claimed is:

1. A process for preparing a pyridine-benzimidazole compound of formula I:

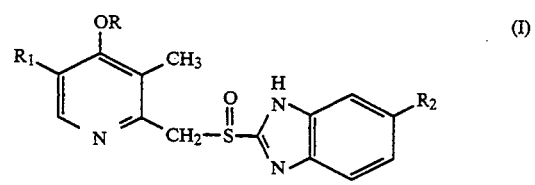

in which either (a) R and R1 are each methyl and R2 is methoxy;, or (b) R is 1,1,1-trifluoroethyl and R1 and R2 are both hydrogen, which comprises oxidizing an amide of the formula (II):

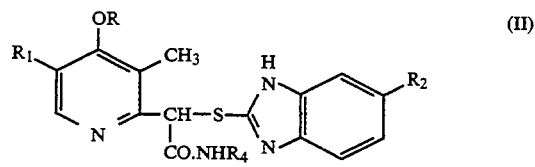

to produce the corresponding amide sulfinyl compound, subjecting the amide sulfinyl compound so formed to alkaline hydrolysis to form a sulfinyl carboxylate, or a salt thereof, of formula (III):

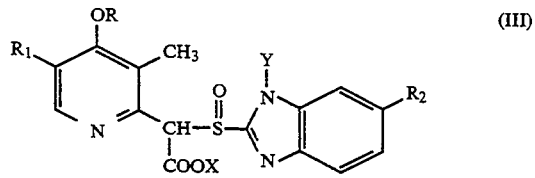

in which X is an alkali metal, Y is hydrogen or a metal, or X and Y together represent a divalent alkaline earth metal; and decarboxylating the sulfinyl carboxylate of formula (III) to form the sulfoxide compound of formula (I), the groups R, R1, and R2 in formulae (II) and (III) having the same meanings as given above, and the group R3 in formula (II) representing hydrogen, lower alkyl or aryl-lower alkyl, optionally further substituted by other functionality to assist in the hydrolysis step.

2. The process of claim 1 wherein the decarboxylation step takes place under weakly acidic conditions, neutral conditions or weakly alkaline conditions.

3. The process of claim 2, wherein the decarboxylation step takes place under non-acidic conditions.

4. The process of claim 3, wherein the oxidation step takes place using hydrogen peroxide as oxidizing agent, over an organic vanadium compound as catalyst.

5. The process of claim 4, wherein the organic vanadium compound is vanadyl acetylacetonate.

6. The process of claim 2, wherein radicals R and $R^1$ are each methyl and radical $R^2$ is methoxy, in the general formulae, so as to produce omeprazole.

* * * * *